United States Patent [19]

Christ et al.

[11] Patent Number: 5,262,097
[45] Date of Patent: Nov. 16, 1993

[54] METHODS FOR ATTACHING FIXATION MEMBERS TO OPTICS OF INTRAOCULAR LENSES

[75] Inventors: F. Richard Christ, Laguna Beach; James E. Francese, Anaheim; Bernard F. Grisoni, Aliso Viejo, all of Calif.

[73] Assignee: Allergan, Inc., Irvine, Calif.

[21] Appl. No.: 824,556

[22] Filed: Jan. 23, 1992

Related U.S. Application Data

[63] Continuation-in-part of Ser. No. 547,859, Jul. 3, 1990, Pat. No. 5,147,397.

[51] Int. Cl.⁵ .................................................. B29D 11/00
[52] U.S. Cl. ........................................ 264/1.4; 264/1.7; 264/22; 264/81; 427/491; 427/255.1; 623/6
[58] Field of Search .......................... 427/491, 255.1; 264/1.4, 1.7, 22, 81; 623/6

[56] References Cited

U.S. PATENT DOCUMENTS

| | | |
|---|---|---|
| 3,776,829 | 12/1973 | Goan . |
| 3,994,027 | 11/1976 | Jensen et al. . |
| 4,025,965 | 5/1977 | Siegmund . |
| 4,104,339 | 8/1978 | Fetz et al. . |
| 4,212,719 | 7/1980 | Osada et al. . |
| 4,307,043 | 12/1981 | Chase et al. . |
| 4,312,575 | 1/1982 | Peyman et al. ................. 427/491 |
| 4,499,148 | 2/1985 | Goodale et al. . |
| 4,502,163 | 3/1985 | Graham . |
| 4,609,420 | 9/1986 | Aydin et al. . |
| 4,615,702 | 10/1986 | Koziol et al. . |
| 4,619,662 | 10/1986 | Juergens, Jr. . |
| 4,662,882 | 5/1987 | Hoffer . |
| 4,668,446 | 5/1987 | Kaplan et al. . |
| 4,701,288 | 10/1987 | Cook et al. . |
| 4,702,865 | 10/1987 | Koziol et al. . |
| 4,718,905 | 1/1988 | Freeman . |
| 4,737,322 | 4/1988 | Bruns et al. . |
| 4,743,327 | 5/1988 | DeHaan et al. . |
| 4,790,846 | 12/1988 | Christ et al. . |
| 4,834,751 | 5/1989 | Knight et al. . |
| 4,854,999 | 8/1989 | Shirmer . |
| 4,888,013 | 12/1989 | Ting et al. . |
| 4,936,846 | 6/1990 | Knoll et al. . |
| 5,026,395 | 6/1991 | Nakajima et al. . |
| 5,069,926 | 12/1991 | Iwata et al. ................. 427/491 |
| 5,080,924 | 1/1992 | Kamel et al. ................. 427/491 |
| 5,104,590 | 4/1992 | Blake . |
| 5,118,452 | 6/1992 | Lindsey et al. . |
| 5,126,164 | 6/1992 | Okazaki et al. . |
| 5,185,107 | 2/1993 | Blake . |

FOREIGN PATENT DOCUMENTS

| | | |
|---|---|---|
| 61-141705 | 6/1986 | Japan ................. 427/491 |
| WO9004512 | 5/1990 | PCT Int'l Appl. . |
| WO9200708 | 1/1992 | PCT Int'l Appl. . |
| 2180757 | 4/1987 | United Kingdom . |

OTHER PUBLICATIONS

Chawla, A. S., Use of Plasma Polymerization for Preparing Silicone-Coated Membranes for Possible Use in (List continued on next page.)

Primary Examiner—Jeffery Thurlow
Assistant Examiner—Mathieu Vargot
Attorney, Agent, or Firm—Gordon L. Peterson

[57] ABSTRACT

New intraocular lenses, fixation member assemblies for use in such lenses and methods for making the same. In one embodiment, the present invention involves a method for producing a fixation member assembly which includes exposing a fixation member component to a first plasma at conditions effective to enhance, relative to a substantially identical fixation member component which is not subjected to the exposing step, the bondability between the fixation member component and a polymeric coating to be located on the fixation member component; and exposing the fixation member to a second plasma in the presence of at least one material selected from polymeric components, polymerizable components and mixtures thereof at conditions effective to form the polymeric coating located on the fixation member component. Enhanced bondability between the polymeric coating-containing fixation member component and the optic of the intraocular lens and/or enhanced biocompatibility are preferably provided.

13 Claims, 2 Drawing Sheets

OTHER PUBLICATIONS

Blood Oxygenators, Artificial Organs vol. 3, No. 1, 1979.

Evans et al, Introduction of Functional Groups onto Carbon Electrodes via Treatment with Radio-Frequency Plasmas, Analytical Chemistry, vol. 51 No. 3, 1979.

Donnet et al, Plasma Treatment Effect on the Surface Energy of Carbon and Carbon Fibers, Carbon vol. 24, No. 6, pp. 757–770, 1986.

Sipehia et al, Enhanced albumin binding to polypropylene beads via anhydrous ammonia gaseous plasma, Biomaterials 1986, vol. 7, Nov., pp. 471–473.

Sakata et al, Corona-Induced Graft Polymerization of Ethyl Acrylate onto Cellulose Film, Journal of Applied Polymer Science, vol. 20, 573–579 (1976).

Wrobel et al, Polymerization of Organosilicones in Microwave Discharges, J. Macromol, Sci. Chem. A14(3), pp. 321–337 (1980).

Suzuki, et al, Graft Copolymerization of Acrylamide onto a Polyethylene Surface Pretreated with a Glow Discharge, Macromolecules 1986, 19, 1804–1808.

Cormia, et al, Use Plasmas to Re-engineer Your Advanced Materials R&D Magazine, Jul. 1990, pp. 60–64.

Osada et al, Plasma-Initiated Graft Polymerization of Water-Soluble Vinyl Monomers Onto Hydrophobic Films and Its Application To Metal Ion Adsorbing Films, Thin Solid Films,118(1984)197–202.

METHODS FOR ATTACHING FIXATION MEMBERS TO OPTICS OF INTRAOCULAR LENSES

RELATED APPLICATION

This application is a continuation-in-part of application Ser. No. 547,859, filed Jul. 3, 1990, now U.S. Pat. No. 5,147,39 which is incorporated in its entirety herein by reference.

BACKGROUND OF THE INVENTION

The present invention relates to intraocular lenses and to fixation member assemblies for use in such lenses. More particularly, the present invention relates to such intraocular lenses and fixation member assemblies which provide enhanced bonding strength between the components of the lenses and assemblies and/or have enhanced biocompatibility.

The use of intraocular lenses (IOLs) to improve vision and/or to replace damaged or diseased natural lenses in human eyes, particularly natural lenses impaired by cataracts, has attained wide acceptance. Accordingly, a variety of IOLs has been developed for surgical implantation in the posterior or anterior chambers of the eye according to a patient's needs.

Known IOLs comprise an optical lens portion or optic which includes an optical zone, and one or more, for example two, supporting structures, called fixation members, for example, loops or haptics, for contacting eye tissue to fix or hold the IOL in the proper position after implantation. The optic may comprise a soft, resilient material, such as any of a variety of flexible elastomers, or a relatively hard or rigid material such as, for example, polymethylmethacrylate (PMMA). The fixation members may comprise a filament constructed of resilient metal or polymeric substance, such as polymethylmethacrylate (PMMA) or polypropylene.

Each of the filament fixation members is preferably flexible to reduce trauma to sensitive eye structures and to be yielding during insertion of the IOL. In addition, filament fixation members generally have a memory retaining capability, e.g., springiness, so that after implantation of an associated IOL, the filament fixation members automatically tend to return to their normal orientations.

As an alternative to filament fixation members, some IOLs are provided with footplate-type fixation members. These footplates generally extend radially outwardly from the optic (for example, in the plane of the optic) and terminate in rounded or blunted ends configured for placement in an eye chamber. The materials for such footplates have included soft materials, for example, 2-hydroxyethyl methacrylate or silicone.

Although the filament fixation members are preferred over the footplate-type fixation members for several reasons, certain difficulties remain. For example, filament fixation members and soft or deformable optics tend to be formed from dissimilar materials which do not ordinarily chemically bond together. As a result, filament fixation members have been designed having a variety of attachment end configurations or structures, e.g., anchor structures for providing a physical interlock between the haptic and optic. Polypropylene fixation members, for example, have heretofore been secured into silicone polymer-based optics by means of a mechanical lock. This lock may comprise a small loop or other anchor formed at the attachment end of the haptic through and/or around which the silicone-based optic precursor material is poured or molded and then cured. Christ et al U.S. Pat. No. 4,790,846 discloses the molding of an optic around a fixation members having a small loop or other anchor to effect a secure fixation members connection.

Christ et al U.S. Pat. No. 4,790,846 further discloses a method for making an IOL in which a region of an elongated filament haptic has a different configuration, e.g., a bulbous enlargement, which cooperates with the optic of the IOL to form a mechanical interlock between this different configuration and the optic and to attach to the optic. If desired, the bulbous enlargement may have its outer surface roughened to improve adhesion of the material of the optic.

Koziol, et al U.S. Pat. Nos. 4,615,702 and 4,702,865 disclose a one-piece haptic structure which comprises an annular loop portion for surrounding the optical pathway or zone through the optic, and having a pair of mounting arms extending radially outwardly from the loop. The loop is embedded within the optic during molding and polymerization of the optic to provide a mechanical interfit. However, the loop can be aesthetically displeasing, and can interfere with peripheral sight through the optic. In addition, the optic is difficult to fold (for the purpose of placing the lens in the eye) without cracking or breaking the loop. Also, due to the lack of chemical interaction between the haptic and the optic, gaps can form at the haptic-optic interface which further impair the optical integrity of the optic.

Kaplan et al U.S. Pat. No. 4,668,446 discloses an alternative method of attaching haptics to the optic of an IOL wherein an enlarged attachment end of the haptic is secured in the optic. This method involves an ethanol induced swelling of a bore hole in the optic, insertion of the enlarged end of the haptic into this bore hole, and removal of the ethanol to shrink the bore hole around the enlarged end of the haptic, thereby producing a mechanical anchoring.

One additional disadvantage of certain fixation members is that they may not be suitably biocompatible, for example, with the ocular tissue which is present when the IOL is in use. The use of biocompatible coatings on such fixation members has an additional disadvantage that such coatings tend to disassociate from the base fixation member.

Freeman U.S. Pat. No. 4,718,905 discloses an IOL including an optic composed of PMMA and haptic loops fashioned from polypropylene strand material. Each haptic strand is coated, using ion beam implantation, with a biocompatible protective ion coating of nitrogen, carbon, silicon or aluminum to protect it from the bioerodable effects of ocular tissue. This patent does not teach, or even suggest, other protective coatings or enhanced haptic-optic bonding. Also, there is no teaching that the haptic loop is subjected to ion beam implantation prior to being secured to the optic.

Notwithstanding these known structures and methods, there remains a need for a method of efficiently and effectively providing structurally durable, biocompatible fixation members which can be secured to the optic of an IOL, preferably without the use of mechanical interlocking structures, so that the fixation member-optic bond is sufficient to resist detachment of the fixation member under normal implantation and wear conditions.

The use of gas plasmas to activate and/or add functional groups to surfaces of fibers is known. For example, see: "Plasma Treatment Effect in the Surface Energy of Carbon and Carbon Fibers", J. B. Donnet, et al, Carbon, Vol. 24, No. 6 pp 757-770 (1986); and "Introduction of Functional Groups Onto Carbon Electrode Via Treatment With Radio-Frequency Plasma", J. F. Evans, et al, Analytical Chemistry, Vol. 51, No. 3, pp 358-365 (1979). Further, Goan U.S. Pat. No. 3,776,829 discloses reacting carbon fibers with ammonia plasma to form amino groups on the fiber surfaces. The amine groups act as cross linking agents for an epoxy resin matrix in the preparation of sized fibers, pre-impregnated tapes, and compositions containing the fibers. None of these documents teach or suggest anything regarding IOLs, let alone enhancing the bondability between fixation members and optics of IOLs.

SUMMARY OF THE INVENTION

New intraocular lenses, fixation member assemblies and methods for making the same have been discovered. The present fixation member assemblies include coatings which are strongly bonded to the base fixation member so as to resist being disassociated from the IOL during use. Further, these coatings preferably provide substantial biocompatibility, more preferably enhanced biocompatibility, and/or enhanced bond strength between the optic and fixation member assembly or assemblies of the present IOLs. Such substantial advantages are achieved using fixation members which preferably have no enlarged structures designed to mechanically lock the fixation member to the optic. The fixation members are more preferably of the filament type in which a portion of the filament is bonded into the optic. Such relatively simple fixation members are effective to fix the position of the IOL in the eye, while reducing, or even eliminating, interference with the optical field or zone of the optic. The present enhanced fixation member assemblies are particularly useful with optics constructed of soft, resilient, deformable materials which can be folded or rolled for insertion through a small incision into the eye.

In one broad aspect of the present invention, methods for producing a fixation member assembly useful as a component in an IOL are provided. In one embodiment, such methods comprise exposing a fixation member component, for example, a standard or conventional filament fixation member, to a plasma in the presence of at least one material selected from polymeric components, polymerizable components and mixtures thereof at conditions effective to form a polymeric coating located on the fixation member component. Using the present method, the polymeric coating, for example, a coating having substantial biocompatability, preferably enhanced biocompatibility relative to the base fixation member component, is strongly bonded to the fixation member component so as to resist becoming disassociated from the fixation member component during use. This coating is preferably more strongly bonded to the fixation member component, that is there is enhanced bondability between this coating and the fixation member component, relative to a substantially similar coating formed without the use of a plasma. There preferably is enhanced bondability between the polymeric coating-containing fixation member component and the optic of the final IOL product relative to a substantially identical fixation member component which has not been so exposed and coated. In a particularly useful embodiment, the fixation member component, prior to being exposed to the above-noted plasma, is exposed to a preliminary or first plasma, preferably an activated gas plasma, at conditions effective to enhance, relative to a substantially identical fixation member component which is not so exposed to this preliminary or first plasma, the bondability between the fixation member component and the polymeric coating to be located on the fixation member component.

In one embodiment, the polymeric coating-containing fixation member component is further exposed to a post-plasma or third plasma at conditions effective to enhance, relative to a substantially identical polymeric coating-containing fixation member component which is not exposed to the post-plasma or third plasma, the bondability between the polymeric coating-containing fixation member component and the optic of the intraocular lens. In this manner, both the strengths of the bonds between the polymeric coating and the base fixation member component, and between the polymeric coating-containing fixation member component and the optic are enhanced, making the final IOL more structurally reliable and durable for long term use in the eye.

In another broad aspect of the invention, methods for producing fixation member assemblies comprise contacting a fixation member component with at least one material selected from polymeric components, polymerizable components and mixtures thereof, for example, in the absence of activating plasma, at conditions effective to coat at least a portion of the fixation member component with the material. This coated fixation member component is exposed to a plasma at conditions effective to enhance, relative to a substantially identical coated fixation member component which is not exposed to the plasma, the bondability between the fixation member component and a polymeric coating derived from the coating located on the fixation member component. This plasma exposing step may also act to enhance the bondability between the polymeric coating-containing fixation member component and the optic of the IOL. The polymeric coating-containing fixation member component has substantial biocompatibility, preferably enhanced biocompatibility relative to the base fixation member component. The polymeric coating-containing fixation member component may be exposed to an additional plasma at conditions effective to enhance the bondability between the polymeric coating-containing fixation member component and the optic of the IOL.

The present invention is further directed to new fixation member assemblies, produced as described herein, for use as components in IOLs. Also, the invention is directed to IOLs which include optics and fixation member assemblies, as described herein.

DETAILED DESCRIPTION OF THE INVENTION

Figure 1:
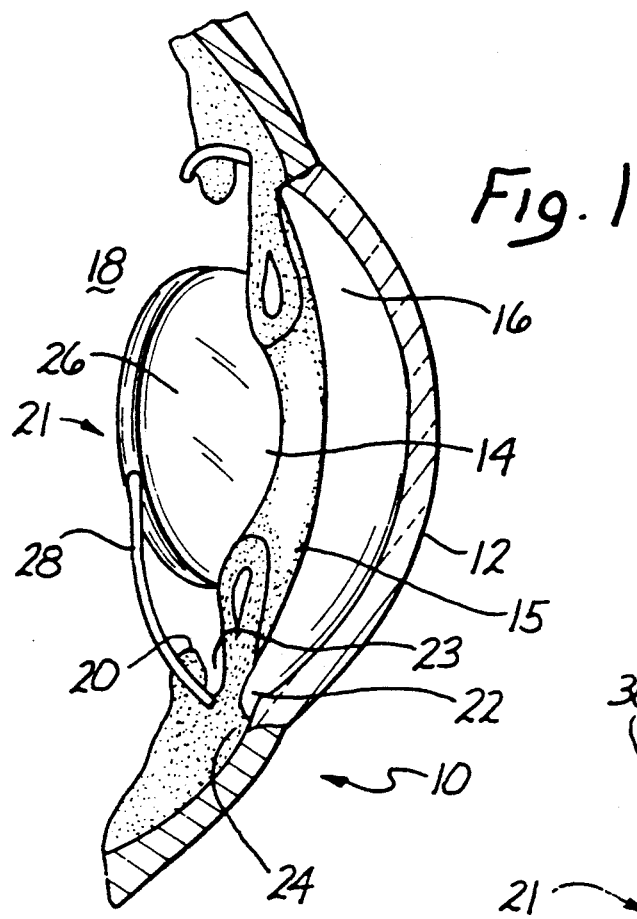
FIG. 1 is a simplified representation of the physiology of the human eye.

Referring to FIG. 1, there is depicted the in vivo placement into an eye 10 of an IOL 21 according to the present invention, in which the loops have been treated, as more particularly described below.

The cornea 12 serves as a refracting medium in addition to its function as the anterior wall of the eye 10. The pupil 14 and the iris 15 of variable aperture are located behind the cornea 12 and divide the eye 10 into an anterior chamber 16 and a posterior chamber 18. The natural crystalline lens (not illustrated) is connected by zonular fibers to a peripheral muscle about the lens known as the ciliary muscle 20.

The surgical implantation of IOL 21 is accomplished by an incision in the eye 10, removal of the diseased, for example, cataractous, or damaged natural lens (if applicable) and insertion of the IOL into the eye. The optic 26 of IOL 21 includes a centrally located optical zone and may be configured for implantation into a specific one or either of the anterior or posterior chambers 16 or 18. The loops 28 of IOL 21 extend radially outwardly in the general plane of the optic 26. In certain embodiments, the loops 28 may be oriented out of the plane of the optic 26, for example, oriented by up to about 10° out of the plane of the optic.

A peripheral limit of anterior chamber angle 22 exists between the base of the iris 15 and a scleral spur, which serves as a support location for IOL 21 implanted within the anterior chamber 16 of the eye 10. A peripheral zone 23 also exists within the posterior chamber 18 between the ciliary muscle 20 and the base of the iris 15, which base is known as the ciliary sulcus 24. This peripheral zone 23 serves as a mounting location for IOL 21 within the posterior chamber 18. Referring to FIG. 1, IOL 21 is shown positioned in the posterior chamber 18 and is supported by the loops 28 bearing upon the ciliary sulcus 24. In certain instances the IOL 21 may be placed in the capsular bag of the eye.

Figure 2:
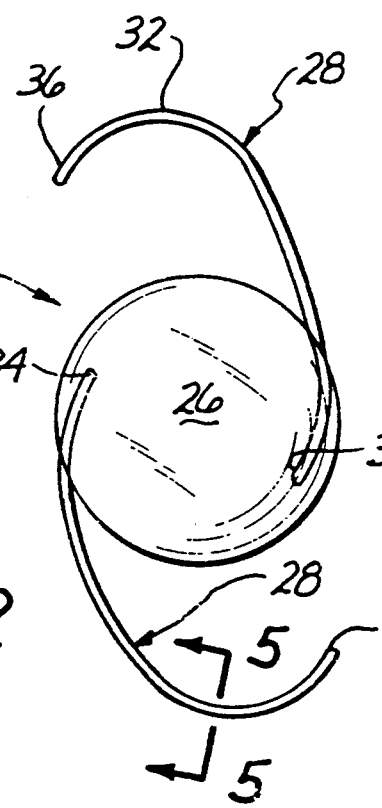
FIG. 2 is a plan view of an IOL in accordance with the present invention.
Figure 5:
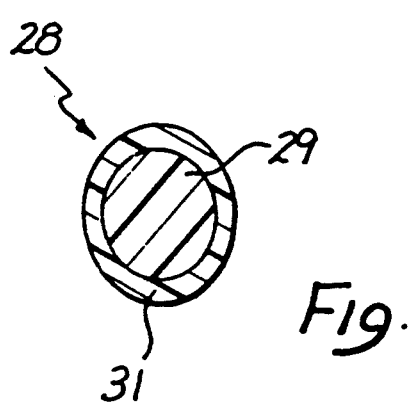
FIG. 5 is a cross-sectional view taken generally along line 5—5 of FIG. 2.
Figure 3:
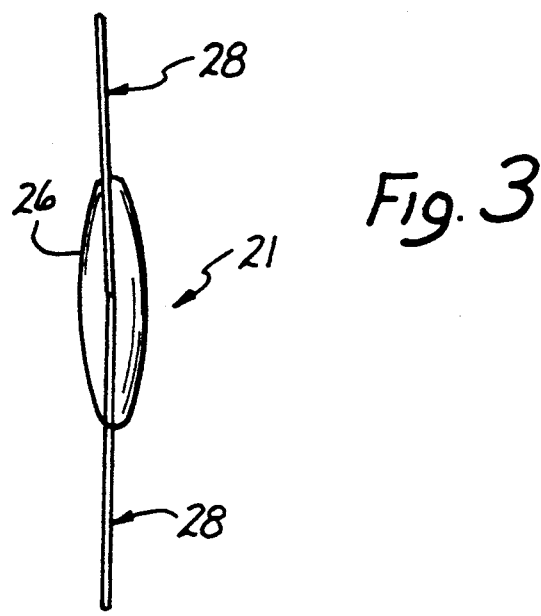
FIG. 3 is a side view of the IOL of FIG. 2.

Referring to FIGS. 2, 3, and 5, IOL 21 is illustrated as including a pair of radially outwardly extending loops 28 secured to optic 26. Each loop 28 includes a base or core loop 29 and a loop coating 31, which substantially surrounds the base loop. Each loop 28 has a substantially uniform cross-section throughout its length and is shown provided with a smoothly curved region 32, intermediate a lens bonding region 34 and a free end region 36. Although the illustrated embodiment is provided with two opposing loops 28, it is understood that an IOL having only one loop or more than two loops bonded to the optic is considered within the scope of the invention.

Typically, each base loop 29 is a flexible member comprising metal or, preferably, polymeric material, and having a substantially circular cross-section, although alternative cross-sectional configurations may be substituted, if desired. The base loops 29 are relatively thin and flexible, while at the same time being sufficiently strong to provide support for IOL 21 in eye 10. The base loops 29 may comprise any of a variety of materials which exhibit sufficient supporting strength and resilience. Suitable materials for this purpose include, for example, polymeric materials such as polypropylene, PMMA, polycarbonates, polyamides, polyimides, polyacrylates, 2-hydroxymethylmethacrylate, poly (vinylidene fluoride), polytetrafluoroethylene and the like; and metals such as stainless steel, platinum, titanium, tantalum, shape-memory alloys, e.g., nitonal, and the like. More preferably, the base loops 29 comprise a polymeric material, in particular selected from polypropylene, PMMA and polyimides, and especially polypropylene. The base loops can be produced using conventional and well known forming techniques. For example, the preferred polymeric base loops can be formed in accordance with known thermoplastic polymer forming techniques, such as by injection molding or by extrusion with subsequent heat forming.

The present invention enables enhanced bonding between dissimilar base loop and optic materials, such as between the preferred polypropylene or PMMA base loops and the preferred silicone polymer-containing optic. The provision of an enhanced bond between loops 28 and optic 26 also reduces the formation of gaps at the interface of the loops 28 and optic 26 which tend to reduce the strength of the loop-optic bond. Each base loop 29 is provided with loop coating 31 which preferably acts to provide an assembly, such as loop 28, with enhanced biocompatibility, in the eye, relative to the base loop. As used herein, the term "biocompatibility" refers to the ability of a thing, for example, an IOL, to perform effectively on a reasonably long term basis in use in an individual's body with no significant detrimental effect on such individual's body.

In accordance with one embodiment of the present invention, enhanced bondability between the loops 28 and the optic 26 is achieved by treating at least appropriate surface regions of the base loops 29 prior to bonding the loops to the optic. The surface of the entire length of each base loop can be treated in accordance with the method disclosed herein. However, if the treatment is designed primarily to achieve enhanced bondability between the loops and the optic, it is preferred to treat only the lens bonding regions or portions of the base loops 29, that is, the regions or portions of the base loops 29 which are intended to be located within the optic 26.

A particularly useful mode of treating each base loop 29 is to expose the base loop to a first plasma at conditions effective to enhance, relative to a substantially identical base loop which is not so exposed, the bondability between the base loop and a polymeric coating, that is, to loop coating 31, which is to be located on the base loop. The base loop 29 is also exposed to a second plasma in the presence of at least one material selected from polymeric components, polymerizable components and mixtures thereof at conditions effective to form a polymeric coating located on the base loop.

The first plasma may have its origin from any of a variety of materials, preferably gases, in particular gases such as oxygen, nitrogen or argon. More preferably, an argon plasma is used. The first plasma is preferably an activated gas plasma.

Methods for generating plasmas are well known in the art, and need not be extensively described here. In general, the base loop 29 is placed in a chamber containing the plasma.

In accordance with one embodiment of the method of the present invention, radio frequency, inductively-coupled first plasma is produced in a plasma chamber by charging the chamber with gas, e.g., argon, preferably at a sub-atmospheric pressure of about 0.01 torr (mm Hg) or greater, more preferably at a pressure in the range of about 0.05 torr to about 0.3 torr. The preferred output power is in the range of about 10 watts to about 500 watts, more preferably about 15 watts to about 120 watts, and still more preferably about 20 watts to about 90 watts.

The base loop 29 is preferably exposed to the first plasma for a period of time in the range of about 1 minute to about 60 minutes, more preferably about 5 minutes to about 60 minutes. However, the specific gas, exposure time, power, and/or other parameters may be varied depending upon the equipment and the particular polymeric coating materials involved, and can be readily optimized based upon the disclosure herein using routine experimentation.

In any event, base loop 29 is exposed to a first plasma at conditions effective to enhance, e.g., relative to a substantially identical base loop which is not so exposed to the first plasma, the bondability between the loop and a polymeric coating to be located on the base loop.

In one embodiment, the first plasma exposed-base loop 29 is preferably then subjected to a second plasma in the presence of one or more polymeric components, polymerizable components and mixtures thereof at conditions effective to form a polymeric coating located on the base loop.

The polymeric components and/or polymerizable components employed in the present second plasma exposing step may be chosen from a wide variety of such components which yield a polymeric loop coating 31 on the base loop having one or more beneficial properties. For example, polymeric loop coating 31 may provide a final loop assembly, loop 28, having enhanced biocompatibility relative to the base loop 29. Also, such loop coating 31 may provide a final loop assembly having enhanced bondability to the optic material of the final IOL product relative to the base loop 29. Thus, the choice of the coating material or materials is dependent, for example, on the base loop material, on the optic material, and on the desired benefit to be obtained from the coating on the base loop. In a particularly useful embodiment, the loop coating 31 on the base loop 29 includes polymeric silicone material, which has a relatively high degree of biocompatibility in the eye. Such polymeric silicone material preferably also acts to provide enhanced loop assembly/optic bondability, particularly where, as is preferred, the optic includes polymeric silicone material.

The second plasma exposing step preferably occurs in the presence of at least one polymerizable component since polymerization in the presence of the second plasma is particularly effective in bonding the base loop to the polymeric coating. In any event, the presence of the second plasma during the formation of the polymeric coating on the base loop enhances the bondability between the polymeric coating and the base loop relative to forming the polymeric coating in the absence of the second plasma.

The second plasma can be a radio frequency, inductively-coupled plasma produced in a plasma chamber by charging the chamber with the component or components for which the polymeric coating is derived, preferably at a sub-atmospheric pressure of about 0.01 torr (mm Hg) or greater, more preferably at a pressure in the range of about 0.05 torr to about 0.3 torr. The preferred output power is in the range of about 10 watts to about 500 watts, more preferably about 15 watts to about 120 watts and still more preferably about 20 watts to about 90 watts.

The base loop 29 is preferably exposed to the second plasma for a period of time in the range of about 1 minute to about 60 minutes more preferably about 5 minutes to about 60 minutes. In addition, if desired, one or more gases, such as those described previously with regard to the first plasma, may be included in the second plasma exposing step. The specific components included in the second plasma exposing step, the exposure time, power and/or other parameters may be varied depending upon the equipment and the particular base loop and optic materials involved, and can be readily optimized based upon the disclosure herein using routine experimentation.

Examples of polymeric components and polymerizable components useful in the present second plasma exposing step include vinyl active silanes, hydride active silanes, vinyl active siloxanes, hydride active siloxanes, cyclic siloxanes, methacrylic acid esters, acrylic acid esters, vinyl active polymers, hydride active polymers, silicone polymers, polymers derived from methacrylic acid esters, polymers derived from acrylic acid esters and mixtures thereof.

In one useful embodiment, the base loop having a polymeric coating thereon is exposed to a third plasma at conditions effective to enhance, relative to a substantially identical polymeric coating-containing loop which is not exposed to the third plasma, the bondability between the polymeric coating-containing loop and the optic of the IOL in which it ultimately is used. This third plasma exposing step is preferably conducted in a manner similar to that in which the first plasma exposing step is conducted.

In an alternate embodiment of the present invention, a base loop 29 is contacted with one or more polymeric components, polymerizable components or mixtures thereof at conditions effective to coat at least a portion of the base loop with the material. This coated loop is exposed to a plasma, e.g., such as the first plasma noted above, at conditions effective to enhance, relative to a substantially identical coated loop which is not exposed to this plasma, the bondability between the base loop and a polymeric coating derived from the coating located on the loop and form a polymeric coating-containing loop. The plasma generating equipment and conditions used in this plasma exposing step are, in general, similar to those employed in the first plasma exposing step described herein. The specific components included in this plasma exposing step, the exposure time, power and/or other parameters may be varied depending on the equipment and the particular base loop and coating materials involved, and can be readily optimized based upon the disclosure herein using routine experimentation.

After the last plasma exposure, the loop 28 is removed from the plasma chamber and bonded to the optic 26.

The lens bonding regions 34 of the loops 28, which, as described herein, are secured to optic, may be provided with any of a variety of configurations, such as an anchoring loop, an anchoring "T", or other anchor structure, to provide a mechanical interlock with the optic, such as has been done in the prior art. However, although such loop anchor structures contribute to the integrity of the bond between the loop and the optic, the method of the present invention enables the use of simpler and less expensive loops having a lens bonding region with no anchor structure, as illustrated in FIG. 2, while still achieving a loop to optic bond of sufficient strength to prevent detachment of the loop from the optic during handling, implantation and wear.

Bonding of the loop 28 directly to the optic 26 is preferably accomplished within about 48 hours after the last plasma-exposure is completed, more preferably within about 24 hours after the last plasma-exposure is completed, and still more preferably within about 3 hours, in particular about 30 minutes to about 3 hours, after the last plasma-exposure is completed.

Figure 4:
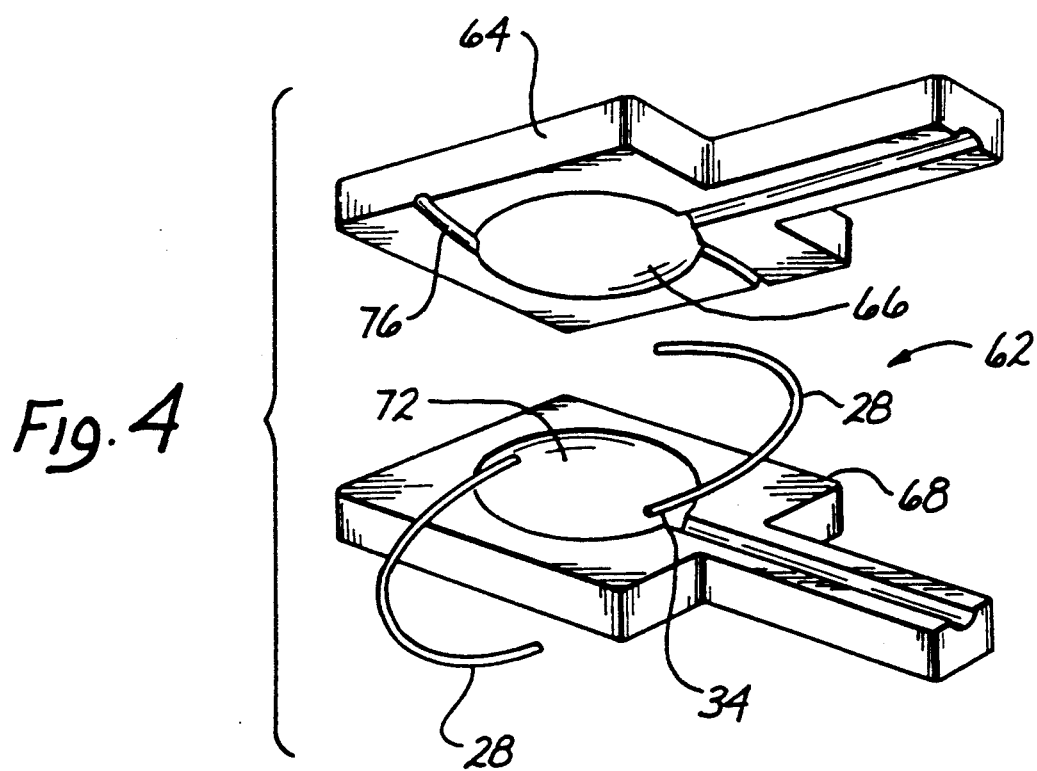
FIG. 4 is a perspective representation of a mold for forming an optic in accordance with the present invention.

Bonding of the loop 28 directly to the optic 26 may be accomplished in a mold 62, such as that illustrated in FIG. 4. The mold 62 comprises an upper plate 64 with an upper concave cavity 66 and a lower plate 68 with a lower concave cavity 72. The upper plate 64 and/or lower plate 68 of the mold 62 are movable relatively toward and away from each other in order to permit insertion of the lens bonding regions 34 of loops 28 therein, introduction of liquid precursor material for forming the optic 26, and removal of the combined optic and haptics (i.e. IOL 21) once the optic is fully cured.

In the illustrated embodiment, the lower plate 68 and upper plate 64 of the mold 62 are each provided with a pair of grooves 76 into and through which the loops 28 are inserted into the combination of upper concave cavity 66 and lower concave cavity 72.

Thus, in forming the IOL 21 in accordance with one embodiment of the invention, the mold plates 64 and 68 are initially separated, and the plasma-exposed loops 28 are positioned in the grooves 76 so that the lens bonding regions 34 are located inside of the combination of upper concave cavity 66 and lower concave cavity 72 when the mold plates 64 and 68 are brought together. Next, a pre-polymer or monomer material, preferably in a viscous liquid form, is introduced into the upper concave cavity 66 and the lower concave cavity 72. Preferably, the pre-polymer or monomer material is introduced in a volume somewhat greater than the sum of the volumes of the two cavities 66 and 72, as is well known in the art, so that it is assured that the combined cavity is completely filled, the excess material being discharged. The mold plates 64 and 68 are then brought together to form the combination of upper concave cavity 66 and lower concave cavity 72, and the pre-polymer or monomer material in this combined cavity is converted into the optic 26, such as by heat curing.

The optic 26 typically comprises an optically suitable and biologically compatible polymer, many of which are known in the art. For example, a two-part silicone formulation may be introduced into the mold cavity at a weight ratio of about 1:1, as is known to one of skill in the art. Part A typically includes a catalyst and a base polymer. Part B typically includes a cross-linker and the same base polymer. The base polymer is preferably synthesized from siloxanes, in particular cyclic siloxanes. Preferably, the optic 26 comprises a polymer which is a platinum-catalyzed, vinyl/hydride addition cured poly (organo siloxane), more preferably incorporating a covalently bonded vinyl-functional benzotriazole for ultraviolet blocking. A particularly useful optic composition includes a silicone-based polymer which is reinforced, for example, with a suitable resin and/or silica.

The optic 26 may comprise materials such as hydrogel-forming polymers, polyphosphazenes, polyurethanes and polyacrylates, as well as silicone polymers, and mixtures thereof, e.g., such as are known in the art. The enhanced loop-optic bond strength of the present invention is particularly advantageous when the optic 26 is constructed of soft, resilient, deformable materials. Rigid optic materials, such as polycarbonates, polysulphones and PMMA, may also be used. In all cases, the particular material should produce an optically clear optic and exhibit biocompatibility in the environment of the eye. Selection parameters for suitable intraocular lens materials are well known to one of skill in the art.

Following introduction into the mold 62, the pre-polymer or monomer material is converted, such as by heat promoted polymerization and/or curing, into a solid or a semi-solid polymer. The conversion may be initiated by any appropriate initiator and/or promotor suitable for the particular pre-polymer or monomer material employed. When the optic precursor material is initially introduced into the mold 62, it surrounds and contacts the lens bonding regions 34 of loops 28 so that the lens bonding regions of the haptics are bonded into the optic after conversion of the optic precursor material.

Alternatively, rather than introducing the prepolymer or monomer material into an open mold 62 and then closing the mold, the mold can be closed after insertion of the lens bonding regions 34 of loops 28 and the pre-polymer or monomer material can then be injected into the combined cavities 66 and 72 under pressure via a suitable input port. Conversion of the pre-polymer or monomer material, as described above, is thereafter accomplished.

In accordance with another embodiment of the method of the present invention, slender inert rods or wires (not illustrated) are introduced into the mold grooves 76 in place of the lens bonding regions 34 of loops 28. Preferably, such rods or wires have substantially the same cross-sectional configuration as the intended loops, and are inserted into the mold 62 to a depth which is approximately equal to the length of the lens bonding regions 34 of the loops 28. In this embodiment, the optic 26 is formed, as previously mentioned, around the portions of the rods or wires extending into the combined cavities 66 and 72. Afterwards the rods or wires are pulled from the optic 26 to produce an optic containing cylindrical recesses extending into the optic for thereafter receiving the lens bonding regions 34 of loops 28.

As a further alternative, the optic 26 may be formed, e.g., molded or cut and/or otherwise machined from a larger mass of polymeric material, without loops or recesses. The optic 26 is subsequently provided with one or more recesses for receiving one or more loops 28. These recesses may be produced in a variety of ways known to one of skill in the art. For example, the recesses can be created using a laser or a needle punch.

Either of the two immediately preceding embodiments of the present invention results in an optic 26 having loop-receiving recesses therein. The loops 28 may thereafter be secured into the recesses by a variety of methods, such as by using a bonding substance or curable composition for bonding the loops in the optic.

Substances useful to bond the loops 28 to the optic 26 include curable or polymerizable monomeric and/or polymeric compositions which can be bonded to both the polymeric coating-containing loops and the optic, and which preferably form covalent bonds with both such polymeric coatings and the polymeric optic materials. In one embodiment, a curable composition capable of forming a polymeric material having substantially the same or a similar chemical composition as the polymer material of the optic 26 and/or as the polymeric material coated on the loops 28 is used. For example, silicone-based curable compositions may be used which, when polymerized, are substantially the same as or similar to the preferred flexible polymer of the optic 26. Such curable compositions are placed in the recess or recesses of optic 26 along with the coated loops 28 and the curable material is cured, such as by the application of heat, to bond the loops 28 to the optic 26. Either as an alternative to, or in addition to, the use of a separate curable composition, the material of the optic 26 may be only partially cured at the time of insertion of the plasma-exposed loops 28. The material is thereafter completely cured, such as by the application of heat, to form a bond between the optic 26 and the loops 28.

The following non-limiting examples illustrate certain aspects of the present invention.

EXAMPLE 1

Comparative

A series of slabs of silicone elastomeric material were prepared by molding a curable composition with the following chemical make-up:

|  | wt % |
|---|---|
| Platinum-containing catalyst | 0.1 |
| Dimethyl Diphenylsiloxane | 78 |
| Silica (reinforcing) | 20 |
| Cross-linking agent | 1.2 |
| Ultraviolet light absorber | 0.7 |

This composition was placed in a mold which was heated to about 150° C. for 6 minutes to cure the composition. Each of the final slabs had a thickness of about 0.079 inches.

A series of extruded PMMA fibers, 0.006 inches in diameter, were selected for testing. None of the fibers used in this Example 1 were exposed to any plasma.

In the first test, which was run three (3) times, the fibers were inserted into the side of one of the slabs to a depth of about 0.080 inches. After insertion, the slab/fiber assemblies were heated to 60° C. for two (2) hours.

In the second test, the fibers were dipped into the above-noted composition for 5 or 10 seconds and then each was immediately inserted into the side of one of the slabs to a depth of about 0.080 inches. After insertion, the slab/fiber assemblies were heated to 60° C. for two (2) hours.

In the third test, which was run two (2) times, the slabs used were prepared (molded) with a hole in the side of the slab about 0.020 inches in diameter and about 0.080 inches deep. Such hole was formed by appropriately placing a pin in the mold during the curing process. The fibers used in this test were dipped into the above-noted composition for 5 or 10 seconds and then each was immediately inserted into the hole in a slab. After insertion, the slab/fiber assemblies were heated to 60° C. for two (2) hours.

After the test specimens had been prepared, each of them was tested as follows. Using a Chatillon tensile tester, the fibers were pulled from the slabs at 2 inches per minute, and the pull force required to achieve this separation was recorded.

Throughout the Examples, at least five test specimens were prepared and tested using the same treatment method and testing procedure. The results provided herein represent the average of the results obtained on the individual test specimens.

Results of these tests were as follows:

|  | PULL FORCE gms. | PULL FORCE gms./0.001 in. inserted[1] |
|---|---|---|
| First test | 70 ± 7 | 0.88 |
|  | 80 ± 2 | 1.00 |
|  | 57 ± 7 | (not measured) |
| Second test | 78 ± 8 | 0.98 |
| Third test | 41 ± 2 | 0.48 |
|  | 50 ± 12 | 0.63 |

[1] Since these were prototype experiments, the depths to which the fibers were inserted varied slightly from specimen to specimen. The pull strength per unit depth inserted is a useful measure of the strength of the slab/fiber bond which is independent of the actual insertion depth.

These tests are to be used as a comparison or control for tests presented hereinafter. Note that dipping the fiber in the curable liquid composition had no substantial advantageous effect on the pull strength of the slab/fiber bond in these tests. Further, using a preformed hole in the slab did not advantageously increase, and may have decreased, the pull strength of the slab/fiber bond.

EXAMPLES 2-6

Example 1 was repeated except that the fibers were subjected to the following pretreatment.

These fibers were first exposed to an argon plasma at 25 watts power, and a pressure of 0.1 torr for about 5 minutes. The plasma generator used was that sold by RF Plasma Products, Inc. under the trademark RF-S. After this plasma treatment, the fibers were held at ambient conditions for 12 to 18 hours or more before being further processed.

After being processed in accordance with Example 1, some of these fibers (Examples 2A and 2B) were further subjected to a plasma at 25 watts power, and a pressure of 0.1 torr for about 10 minutes in the presence of 1,3,5-trivinyl-1,1,3,5,5-pentamethyltrisiloxane. Afterwards, these fibers were included in slab/fiber assemblies (first test and third test), which assemblies were tested for pull strength.

After being processed in accordance with Example 1, some of these fibers (Examples 3A and 3B) were further subjected to a plasma at 25 watts powers, and a pressure of 0.1 torr for about 10 minutes in the presence of 1,1,3,3-tetravinyldimethyldisiloxane. Afterwards, these fibers were included in slab/fiber assemblies (first test and third test), which assemblies were tested for pull strength.

After being processed in accordance with Example 1, some of these fibers (Examples 4A and 4B) were further subjected to a plasma at 25 watts power, and a pressure of 0.1 torr for about 10 minutes in the presence of argon and vinyltrimethylsilane. Afterwards, these fibers were included in slab/fiber assemblies (first test and third test), which assemblies were tested for pull strength.

After being processed in accordance with Example 1, some of these fibers (Examples 5A and 5B) were further processed as outlined in the immediately preceding paragraph except that the duration of the plasma treatment was 20 minutes. Afterwards, these fibers were included in slab/fiber assemblies (first test and third test), which assemblies were tested for pull strength.

After being processed in accordance with Example 1, some of these fibers (Examples 6A, 6B, and 6C) were further processed as outlined in the immediately preceding paragraph except that the duration of the plasma treatment was 30 minutes. Afterwards, these fibers were included in slab/fiber assemblies (first, second and third tests), which assemblies were tested for pull strength.

Results of these pull strength tests were as follows:

| Example | PULL FORCE, gms. | PULL FORCE, gms./.001 in. inserted |
|---|---|---|
| 2A (First test) | 60 ± 9 | 0.74 |
| 2B (Third test) | 86 ± 16 | 0.99 |
| 3A (First test) | 70 ± 9 | 1.07 |
| 3B (Third test) | 124 ± 8 | 1.70 |
| 4A (First test) | 83 ± 8 | 1.27 |
| 4B (Third test) | 115 ± 13 | 1.72 |
| 5A (First test) | 73 ± 3 | 1.12 |
| 5B (Third test) | 143 ± 18 | 2.23 |
| 6A (First test) | 70 ± 7 | 0.92 |
| 6B (Second test) | 81 ± 11 | 1.16 |
| 6C (Third test) | 90 ± 11 | 1.06 |

These results indicate that subjecting the fibers to a plasma in the presence of a polymerizable component often provides increased bond strength relative to fibers which are bonded to the slabs without being exposed to such plasma (Example 1). Note the substantial increase in pull force (in terms of force per insertion depth) required in Examples 3A, 4A and 5A compared with the first tests of Example 1. Especially useful bond strength benefits are achieved if such fibers, after this plasma treatment, are dipped in a curable liquid prior to being inserted in the slabs. This can be seen by comparing Examples 3B, 4B, 5B, 6B, and 6C with the second and third tests of Example 1. In addition, the coated fibers produced in Examples 2 to 6 have sufficient biocompatibility so as to be useful in the eye as components of IOLs.

While this invention has been described with respect to various specific examples and embodiments, it is to be understood that the invention is not limited thereto and that it can be variously practiced within the scope of the following claims.

What is claimed is:

1. A method for attaching a fixation member to an optic of an intraocular lens comprising:
    exposing a fixation member component to a plasma in the presence of at least one material selected from the group consisting of polymeric components, polymerizable components and mixtures thereof at conditions effective to form a polymeric coating located on said fixation member component; and
    securing said fixation member component with said polymeric coating located thereon in a polymeric intraocular lens optic component, the bondability between said fixation member component with said polymeric coating located thereon and said polymeric intraocular lens optic component being enhanced relative to a substantially identical fixation member component which is not exposed to any plasma.

2. The method of claim 1 wherein said at least one material is selected from the group consisting of silanes, siloxanes, methacrylic acid esters, acrylic acid esters, silicone polymers, polymers derived from methacrylic acid esters, polymers derived from acrylic acid esters, and mixtures thereof.

3. The method of claim 1 wherein said securing step comprises:
    providing said polymeric intraocular lens optic component with a recess;
    placing a curable composition and a portion of said fixation member component with said polymeric coating located thereon in said recess; and
    curing said curable composition.

4. The method of claim 1 which further comprises exposing said fixation member component to a preliminary plasma at conditions effective to enhance, relative to a substantially identical fixation member component which is not subjected to said preliminary plasma exposing step, the bondability between said fixation member component and said polymeric coating to be located on said fixation member component.

5. The method of claim 1 which further comprises exposing said fixation member component with said polymeric coating located thereon to a post-plasma at conditions effective to enhance, relative to a substantially identical polymeric coating-containing fixation member which is not subjected to said post-plasma exposing step, the bondability between said fixation member component with said polymeric coating located thereon and said polymeric intraocular lens optic component.

6. The method of claim 5 wherein said securing step comprises:
    providing said polymeric intraocular lens optic component with a recess;
    placing a curable composition and a portion of said fixation member component with said polymeric coating located thereon in said recess; and
    curing said curable composition.

7. The method of claim 4 which further comprises exposing said fixation member component with said polymeric coating located thereon to a post-plasma at conditions effective to enhance, relative to a substantially identical polymeric coating-containing fixation member which is not subjected to said post-plasma exposing step, the bondability between said fixation member component with said polymeric coating located thereon and said polymeric intraocular lens optic component.

8. The method of claim 7 wherein said securing step comprises:
    providing said polymeric intraocular lens optic component with a recess;
    placing a curable composition and a portion of said fixation member component with said polymeric coating located thereon in said recess; and
    curing said curable composition.

9. The method of claim 1 wherein said at least one material is organic.

10. The method of claim 1 wherein said exposing occurs at sub-atmospheric pressure.

11. The method of claim 4 wherein said securing step comprises:
    providing said polymeric intraocular lens optic component with a recess;
    placing a curable composition and a portion of said fixation member component with said polymeric coating located thereon in said recess; and
    curing said curable composition.

12. The method of claim 4 wherein said preliminary plasma exposing step occurs at sub-atmospheric pressure.

13. The method of claim 5 wherein said post-plasma exposing step occurs at sub-atmospheric pressure.

* * * * *